(12) United States Patent
Smith et al.

(10) Patent No.: US 10,188,645 B2
(45) Date of Patent: Jan. 29, 2019

(54) METHODS AND COMPOSITIONS FOR AMELIORATING SYMPTOMS OF TERMINATION OF OPIOID PAIN THERAPY

(71) Applicants: Ian Cain Smith, Statesboro, GA (US); Robert W. Mooney, Sanford, NC (US)

(72) Inventors: Ian Cain Smith, Statesboro, GA (US); Robert W. Mooney, Sanford, NC (US)

(*) Notice: Subject to any disclaimer, the term of this patent is extended or adjusted under 35 U.S.C. 154(b) by 0 days.

(21) Appl. No.: 15/249,085

(22) Filed: Aug. 26, 2016

(65) Prior Publication Data

US 2017/0056394 A1 Mar. 2, 2017

Related U.S. Application Data

(60) Provisional application No. 62/210,157, filed on Aug. 26, 2015.

(51) Int. Cl.
*A61K 31/495* (2006.01)
*A61K 31/4155* (2006.01)
*A61K 31/485* (2006.01)
*A61K 31/415* (2006.01)
*A61K 31/4168* (2006.01)
*A61K 31/4178* (2006.01)

(52) U.S. Cl.
CPC ........ *A61K 31/495* (2013.01); *A61K 31/4168* (2013.01); *A61K 31/4178* (2013.01); *A61K 31/485* (2013.01)

(58) Field of Classification Search
None
See application file for complete search history.

(56) References Cited

U.S. PATENT DOCUMENTS

| 8,716,224 | B2 | 5/2014 | Shailubhai et al. |
| 8,729,070 | B2 | 5/2014 | Glozman |
| 8,779,090 | B2 | 7/2014 | Zimmer et al. |
| 9,226,918 | B2 | 1/2016 | Peltz et al. |
| 2007/0072899 | A1* | 3/2007 | Johnson ............... A61K 31/00 514/303 |
| 2010/0144754 | A1* | 6/2010 | Peltz ................... A61K 31/4178 514/255.04 |
| 2011/0212090 | A1 | 9/2011 | Pedersen et al. |
| 2013/0157990 | A1* | 6/2013 | Carpenter ............ A61K 31/137 514/171 |
| 2014/0052051 | A1 | 2/2014 | Tagliaferri et al. |

* cited by examiner

*Primary Examiner* — Bong-Sook Baek
(74) *Attorney, Agent, or Firm* — Troutman Sanders LLP; Alexis Simpson; Tiffany Palmer

(57) ABSTRACT

The disclosure is directed to a method of easing a patient's symptoms related to termination of opioid pain therapy, and compositions for achieving said method. The method and compositions comprise a series of self tapering dosages of a pharmaceutical composition that is configured to alleviate or prevent symptoms of the patient's termination of opioid pain therapy. The series of self tapering dosages may be supplied in a dosage package.

9 Claims, 1 Drawing Sheet

METHODS AND COMPOSITIONS FOR AMELIORATING SYMPTOMS OF TERMINATION OF OPIOID PAIN THERAPY

CROSS-REFERENCE TO RELATED APPLICATIONS

This application claims priority to U.S. Provisional Application No. 62/210,157, filed on 26 Aug. 2015, the disclosure of which is herein incorporated by reference in its entirety.

BACKGROUND

Opioid therapies and treatments, and opiate-based analgesics, have become a critical component in treatment and management of pain in the clinical setting. Associated with those therapies is the well-recognized opioid addiction, which has drawn a great deal of attention and focus. However, what has drawn less attention is the difficulty that even the non-addicted population has when withdrawing from standard accepted patterns of prescribing narcotic pain relieving medications. Experience has shown that a patient recovering from surgery with a take-home opiate prescription will experience physical discomfort complicated by the short term use of pain relievers which contain narcotics. The same is also observed in the office-based use of narcotics for as little as a week. Physicians are well aware of the risks of increasing discomfort when a short term pain prescription ends, and both patient and physician realize that stopping the narcotic is in the best interest of all. However, accomplishing this transition is often difficult, uncomfortable and time-consuming. A gradual decrease in dosage of the narcotic is an accepted solution, however achieving the correct balance of quantity, strength and timing is often outside the realm of patient responsibility.

What is needed, therefore, is a method of ameliorating or preventing a patient's symptoms related to termination of opioid pain therapy, and compositions for achieving said method. The method and compositions should take advantage of knowledge of managing opioid pain therapy termination, yet improve such methods and compositions by providing a series of self tapering dosages of a pharmaceutical composition that is configured to alleviate or prevent symptoms of the patient's termination of opioid pain therapy. It is to such a method and composition that embodiments of the present disclosure are primarily directed.

BRIEF SUMMARY OF THE INVENTION

In one aspect, the present disclosure provides a method of easing a patient's termination of opioid pain therapy comprising administering to the patient a series of self tapering dosages of a pharmaceutical composition, wherein the pharmaceutical composition comprises clonidine, hydroxyzine, ondansetron and naltrexone between at least a first and a second dosage, and wherein the pharmaceutical composition is configured to alleviate or prevent symptoms of the patient's termination of opioid pain therapy.

In one embodiment of the method, the pharmaceutical composition is provided over a time period of five to twenty days.

In another embodiment of the method, the pharmaceutical composition is provided over a time period of seven to ten days.

In yet another embodiment of the method, the pharmaceutical composition comprises at least three of:

0.025 mg to 3 mg clonidine;
25 mg to 100 mg hydroxyzine;
0.5 to 10 mg ondansetron; and
0.25 to 50 mg naltrexone.

In another embodiment of the method, the first dosage is administered at the termination of opioid pain therapy and up to seven days after the termination of opioid pain therapy.

In any of the above embodiments of the method, the second dosage is administered after the last dose of the first dosage, and is administered for at least three days.

In yet another embodiment of the method, a first dosage comprises:

20 mg to 100 mg hydroxyzine;
0.05 mg to 2 mg clonidine; and
2 to 8 mg ondansetron.

In another embodiment of the method, a second dosage comprises:

15 mg to 100 mg hydroxyzine;
0.05 mg to 2 mg clonidine;
2 mg to 8 mg ondansetron; and
0.5 mg to 15 mg naltrexone.

In another aspect, the present disclosure provides a self tapering dosage package, wherein the dosage package comprises a first dosage of a first formulation and a second dosage of a second formulation, wherein the first dosage is administered prior to the second dosage, wherein the first dosage is administered at a patient's termination of opioid pain therapy, and wherein the first and second dosages are configured to alleviate or prevent symptoms of the patient's termination of opioid pain therapy.

In another embodiment of the dosage package, the first dosage comprises a pharmaceutical formulation comprising:

30 mg to 45 mg hydroxyzine;
0.5 mg to 1.0 mg clonidine; and
2 mg to 6 mg ondansetron, and the second dosage comprises a pharmaceutical formulation comprising:

20 mg to 30 mg hydroxyzine;
0.05 mg to 1.0 mg clonidine;
2 mg to 6 mg ondansetron; and
1 mg naltrexone.

In an embodiment of the dosage package, the dosage package includes at least three days of the first dosage.

In yet another embodiment of the dosage package, the dosage package contains at least one first dosage for at least one day.

In an embodiment of any of the foregoing dosage packages, the dosage package includes at least two days of the second dosage.

In an embodiment of any of the foregoing dosage packages, the dosage package contains at least one second dosage for at least one day.

In an embodiment of any of the foregoing dosage packages, the dosage package does not include the first and second dosages on the same day.

In an embodiment of any of the foregoing dosage packages, the first dosage comprises:

20 mg to 100 mg hydroxyzine;
0.05 mg to 2 mg clonidine; and
2 to 8 mg ondansetron.

In an embodiment of any of the foregoing dosage packages, the second dosage comprises:

15 mg to 100 mg hydroxyzine;
0.05 mg to 2 mg clonidine;
2 mg to 8 mg ondansetron; and
0.5 mg to 15 mg naltrexone.

In another aspect, the present disclosure provides a pharmaceutical composition for transitioning a patient from opioid pain therapy comprising at least three of hydroxyzine, clonidine, ondansetron and naltrexone formulated into a single unit dosage, wherein the dosage is administered to a patient at termination of the patient's opioid pain therapy.

In one embodiment, the pharmaceutical composition is configured to alleviate or prevent symptoms of the patient's termination of opioid pain therapy.

In another embodiment, the pharmaceutical composition comprises a series of tapering dosages of at least one of hydroxyzine, clonidine, ondansetron and naltrexone.

In an embodiment of any of the foregoing pharmaceutical compositions, the pharmaceutical composition is provided in a dosage package comprising at least two dosages.

In another embodiment of any of the foregoing pharmaceutical compositions, the first dosage of the pharmaceutical composition comprises hydroxyzine, clonidine and ondansetron.

In yet another embodiment of any of the foregoing pharmaceutical compositions, the second dosage of the pharmaceutical composition comprises hydroxyzine, clonidine, ondansetron and naltrexone.

In another embodiment of any of the foregoing pharmaceutical compositions, the first dosage is administered for at least three days and the second dosage is administered after the last administration of the first dosage for at least two days.

BRIEF DESCRIPTION OF THE DRAWINGS

The accompanying Figures, which are incorporated in and constitute a part of this specification, illustrate several aspects described below.

DETAILED DESCRIPTION OF THE INVENTION

As specified in the Background Section, there is a great need in the art to identify technologies for technologies for managing a patient's symptoms associated with the termination of opioid pain therapy and use this understanding to develop novel methods and compositions for alleviating and/or preventing such symptoms.

Definitions

To facilitate an understanding of the principles and features of the various embodiments of the disclosure, various illustrative embodiments are explained below. Although exemplary embodiments of the disclosure are explained in detail, it is to be understood that other embodiments are contemplated. Accordingly, it is not intended that the disclosure is limited in its scope to the details of construction and arrangement of components set forth in the following description or examples. The disclosure is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

The values disclosed herein are not to be understood as being strictly limited to the exact numerical values recited.

Instead, unless otherwise specified, each such value is intended to mean both the recited value and a functionally equivalent range surrounding that value. For example, a value disclosed as "50 mg" is intended to mean "about 50 mg."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present disclosure are intended to be illustrative and not restrictive. Many suitable materials that would perform the same or a similar function as the materials described herein are intended to be embraced within the scope of the disclosure. Such other materials not described herein can include, but are not limited to, materials that are developed after the time of the development of the disclosure, for example. Any dimensions listed in the various drawings are for illustrative purposes only and are not intended to be limiting. Other dimensions and proportions are contemplated and intended to be included within the scope of the disclosure.

As used herein, the term "subject" or "patient" refers to mammals and includes, without limitation, human and veterinary animals. In a preferred embodiment, the subject is human.

As used herein, the term "combination" of the pharmaceutically active ingredients discussed herein means at least two, but any desired combination of compounds can be delivered simultaneously or sequentially (e.g., within a 24 hour period). It is contemplated that when used to treat various diseases, the compositions and methods of the present disclosure can be utilized with other therapeutic methods/agents suitable for the same or similar diseases. Such other therapeutic methods/agents can be co-administered (simultaneously or sequentially) to generate additive or synergistic effects. Suitable therapeutically effective dosages for each agent may be lowered due to the additive action or synergy.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The terms "ameliorating," "mitigating," "easing" or "preventing" as use herein, unless otherwise specified, mean treating, controlling, preventing, or otherwise reducing the occurrence, severity or relapse of an identified symptom, condition, or disease, in individuals afflicted with or prone to develop such symptoms, condition or disease.

As used herein the term "therapeutically effective" applied to dose or amount refers to that quantity of a compound or pharmaceutical composition that when administered to a subject for treating, preventing, mitigating, diminishing, or ameliorating a state, disorder or condition, is sufficient to effect such treatment. The "therapeutically effective amount" will vary depending on the compound or bacteria or analogues administered as well as the disease and its severity and the age, weight, physical condition and responsiveness of the mammal to be treated.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The phrase "series of self tapering dosages" as used herein refers to at least two pharmaceutical compositions comprising decreasing amounts of at least one of hydroxyzine, clonidine and ondansetron relative to one another and optionally increasing amounts of naltrexone. In some embodiments, a first dosage comprises hydroxyzine, clonidine and ondansetron, while a second dosage comprises hydroxyzine, clonidine, ondansetron and naltrexone. It is further contemplated that the amounts of the drugs may vary within the first and second dosage forms as needed in order to appropriately ameliorate the symptoms of termination of opioid pain therapy, as discussed in more detail herein.

The term "opioid pain therapy" or "opioid pain medication" as used herein refers to pain therapy or management comprising opioid or opiate medications. Such medications include, for example and not limitation, fentanyl (Duragesic), hydrocodone (Vicodin), hydromorphone (Dilaudid), morphine, oxycodone (OxyContin, Percocet, Lorcet), codeine, meperidine, and tramadol.

The phrase "termination of opioid pain therapy" as used herein refers to the termination of administration of opioid pain medications under a physician's direction. The duration of the opioid pain therapy depends on the patient's need, such as for example and not limitation, after surgery, after an injury requiring pain management but not surgery, patients suffering from chronic or acute pain, and further may vary for those patients with a history of, or predisposition to, substance abuse. It is known that the termination of even short-term use of opioid pain medications may cause symptoms such as, for example and not limitation, tachycardia (fast pulse), hypertension, sweats/excessive perspiration, hot and cold flashes, chills, muscle aches, muscle cramps, leg cramps, increase in preexisting pain, back pain, general restlessness, sleeplessness, insomnia, yawning, mood swings, changes in behavior, irritability, general malaise, emotional instability, depression, anxiety, diarrhea, stomach cramping/aches, anorexia, nausea, and/or vomiting. It is further known that the severity of these symptoms may be related to the length of the opioid pain therapy, the dosages of the opioid pain medications used in the therapy, and/or the patient's individual pharmacogenomics or predisposition to substance abuse. Symptom emergence may be rapid, e.g., within 4-12 hours, or more gradual, such as within 2-7 days. Symptoms may appear mild at onset but generally rapidly increase in intensity. Such symptoms may persist in some cases up to 14 to 21 days.

The phrase "at termination of opioid pain therapy" as used herein refers to the time period within about 4 hours after the patient's last dose of the opioid pain medication and about 72 hours after the patient's last dose of the opioid pain medication.

The phrase "single unit dose" as used herein refers to a single pharmaceutical composition comprising at least three of hydroxyzine, clonidine, ondansetron and naltrexone. For example and not limitation, the single unit dosage may comprise hydroxyzine, clonidine and ondansetron compounded into a single tablet or capsule. Alternatively, the single unit dose may comprise hydroxyzine, clonidine, ondansetron and naltrexone compounded into a single tablet or capsule. The single unit dose may further comprise carriers and/or other ingredients as described in more detail herein.

The phrase "alleviating or preventing symptoms associated with termination of opioid pain therapy" as used herein refers to the amelioration, management, alleviation, and/or prevention of a patient's symptoms that occur at the termination of opioid pain therapy. Non-limiting examples of such symptoms include tachycardia (fast pulse), hypertension, sweats, hot and cold flashes, general restlessness, sleeplessness, insomnia, yawning, mood swings, changes in behavior, diarrhea, nausea, and/or vomiting.

The phrase "after the first dosage" as used herein refers to the time period within about one hour after administration of the first dosage to about 48 hours after administration of the first dosage.

The term "dose" as used herein refers to a single unit, or subunit, of the first and/or second dosage. For example, e.g., a dose can be a single tablet or capsule of the first and/or second dosage. A daily dose can be the 24 hour allotment of the first and/or second dosage.

The term "dosage" as used herein refers to a pharmaceutical composition comprising at least three of hydroxyzine, clonidine, ondansetron and naltrexone. In a preferred embodiment, a first dosage comprises hydroxyzine, clonidine and ondansetron. In another preferred embodiment, a second dosage comprises hydroxyzine, clonidine, ondansetron and naltrexone.

The term "formulation" as used herein refers to a dosage in combination with at least one other pharmaceutically acceptable ingredient.

Overview of the Disclosure

The present disclosure is directed to administration of a series of self tapering dosages of a pharmaceutical composition comprising at least three of hydroxyzine, clonidine, ondansetron and naltrexone. It has been found that administering these drugs in combination ameliorates or prevents a patient's symptoms associated with termination of opioid pain therapy. As discussed herein, the severity of the symptoms may vary from patient to patient, and thus administration of the pharmaceutical compositions of the disclosure may be varied accordingly in accordance with the general methods described herein.

The inventors have found that starting the clonidine, hydroxyzine and ondansetron at higher amounts (relative to the amounts administered later in the therapeutic method) serves to control onset of the most acute symptoms. As these symptoms decrease over time, the amounts of clonidine, hydroxyzine and ondansetron are gradually decreased in strength and frequency accordingly. After at least three days of taking the first dosage, dependent upon the patient's symptom severity, the patient begins the second dosage further comprising naltrexone. Naltrexone, as an opiate antagonist, assists in unbinding any remaining opiates from the opiate receptors, which shortens the expected period of withdrawal, and also blocks the patient's opiate receptors so that any further ingestion of opiates will be less effective. The strength of the naltrexone is started at a very low dose to minimize the risk of precipitated withdrawal and is gradually increased throughout the remainder of the treatment cycle. Dosages of naltrexone remain lower than typically suggested strengths in order to add a slight benefit of an antagonist without increasing the patient's discomfort due to symptoms resulting from termination of opioid pain therapy.

The therapeutic methods of the disclosure comprise administration of at least two dosages of a pharmaceutical composition comprising at least three of clonidine, hydroxyzine, ondansetron and naltrexone. In a preferred embodiment, a first dosage comprises clonidine, hydroxyzine and ondansetron. In a preferred embodiment, a second dosage comprises clonidine, hydroxyzine, ondansetron and naltrexone. In a further preferred embodiment, the amounts of one or more of clonidine, hydroxyzine and ondansetron in the first dosage are higher than the amounts of clonidine, hydroxyzine and ondansetron in the second dosage. The first dosage does not contain naltrexone, while the second dosage comprises increasing amounts of naltrexone.

It is further contemplated herein that amounts of clonidine, hydroxyzine and ondansetron may vary across the first dosage, and specifically may decrease across the first dosage such that the pharmaceutical composition administered on the first day of the first dosage of the self taper has a higher amount of at least one of clonidine, hydroxyzine and ondansetron relative to the pharmaceutical composition administered on the last day of the first dosage of the self taper.

As discussed above, it is known that the severity and type of the patient's symptoms is variable, and that the onset and duration of the symptoms is also variable. The therapeutic methods of the disclosure are able to take this variation into account when providing appropriate pharmaceutical compositions to ameliorate such symptoms. For example and not limitation, it is possible to take patient-to-patient variation in symptom severity into account by one or more of the following: (i) administering the first and second dosages for varying lengths of time; (ii) administering more than one dose of the first and/or second dosage per day; and (iii) tapering the amounts of one or more of clonidine, hydroxyzine, ondansetron and naltrexone within the same dosage. Therefore, a patient who has more severe symptoms may:

(i) receive a first and/or second dosage that is administered for a longer period of time than a patient with less severe symptoms (e.g., the patient may (i) receive at least two dosages for a longer time period; (ii) receive a first dosage for a longer time period; and/or (iii) may receive a second dosage for a longer time period);

(ii) receive more than one dose of the first and/or second dosage per day (e.g., the patient may take multiple doses of the first dosage on the first day of treatment with the invented methods, and then decrease the number of doses per day of the first dosage over time); and/or (iii) receive a first dosage with a higher amount of one or more of clonidine, hydroxyzine, ondansetron, which amount decreases during the period of administration of the first dosage; and/or receive a second dosage with a higher amount of one or more of clonidine, hydroxyzine, ondansetron and naltrexone, which amount decreases during the period of administration of the second dosage.

In one aspect of the present disclosure, the method comprises administration of a series of self tapering dosages of a pharmaceutical composition, wherein the pharmaceutical composition comprises clonidine, hydroxyzine, ondansetron and naltrexone between at least a first and a second dosage, and wherein the pharmaceutical composition is configured to alleviate or prevent symptoms of the patient's termination of opioid pain therapy.

In one aspect, the medications disclosed herein in the method, dosage packages and pharmaceutical compositions can include clonidine. Clonidine is an $\alpha_2$-agonist used commonly in blood pressure medication which has been used to alleviate symptoms of elevated pulse and blood pressure, anxiety and some musculoskeletal discomfort, as well as mild insomnia. Clonidine can be present in a dose of the present disclosure from about 0.025 to about 3 mg, from about 0.025 to about 2 mg, from about 0.05 to about 2 mg, from about 0.05 to about 1 mg, or from about 0.05 to about 0.5 mg.

In another aspect, the medications disclosed herein in the method, dosage packages and pharmaceutical compositions can include hydroxyzine. Hydroxyzine is an antihistamine historically used for control of allergy symptoms, which can alleviate symptoms such as anxiety, insomnia and muscle aches. Hydroxyzine can be present in a dose for the present disclosure from about 5 mg to about 100 mg, from about 10 mg to about 75 mg, from about 15 to about 50 mg, from about 15 to about 40 mg, from about 20 mg to about 50 mg, or from about 30 mg to about 50 mg.

In another aspect, the medications disclosed herein in the method, dosage packages and pharmaceutical compositions can include ondansetron. Ondansetron is a serotonin 5-HT3 receptor antagonist which can assist with gastrointestinal discomfort such as nausea, vomiting and gastric distress. Ondansetron can be present in a dose for the present disclosure from about 0.5 to about 10 mg, from about 1 to about 10 mg, from about 2 to about 10 mg, from about 1 to about 8 mg, from about 1 to about 6 mg, from about 2 to about 6 mg, from about 3 to about 6 mg, or from about 3 to about 5 mg.

In another aspect, the medications disclosed herein in the method, dosage packages and pharmaceutical compositions can include naltrexone. Naltrexone is an opioid receptor and antagonist traditionally used to block opioids and precipitate withdrawal. In the current composition, it can assist in unbinding any remaining opiates from the opiate receptors which shortens the expected period of withdrawal. Second, it can block the body's opiate receptors so that any further ingestion of opiates will be less effective. The strength of the naltrexone can be started at a very low dose to minimize the risk of precipitated withdrawal and can be gradually increased throughout the remainder of the treatment cycle. Dosages of naltrexone can remain lower than typically suggested strengths in order to add a slight benefit of an antagonist without increasing withdrawal discomfort. Naltrexone can be present in a dose for the present disclosure from about 0.25 to about 50 mg, but preferably lower, such as from about 0.25 to about 15 mg, about 0.25 to about 10 mg, from about 0.5 to about 10 mg, from about 0.5 to about 5 mg, or from about 0.5 to about 2 mg.

As described herein, the number, variety and severity of the symptoms of termination of opioid pain therapy make it difficult for the treating provider to adequately prescribe non-opiate containing medications. It is entirely possible for the provider to inadvertently prescribe non-effective, ineffective, or even conflicting medications, and further to prescribe amounts of medications that are ineffective to treat the patient's symptoms. Recognizing the need in the art for a method and pharmaceutical composition that prevents these problems, the inventors have developed a method of administrating a pharmaceutical composition comprising appropriate amounts of non-opiate and non-controlled medications, as described in more detail herein. In preferred embodiments, the pharmaceutical composition is provided in a format that allows the patient to begin treatment at a higher dose and then taper in a manner that is easily followed over a time frame sufficient to give symptom relief. In an exemplary embodiment, the pharmaceutical composition is provided in a dosage package, wherein each individual dose is separated and labeled for each dosing time throughout the day. The dosage package also institutes a self tapering strategy, such that (i) the number of doses over a period of days can be decreased, (ii) multiple dosages containing different medications can be provided, and/or (iii) the amount of one or more of the medications will gradually change in individual doses throughout the taper to incorporate a gradual tapering of required medication.

Therapeutic Methods of the Disclosure

In one embodiment, the method comprises administration of a first dosage comprising clonidine, hydroxyzine and ondansetron. In another embodiment, the method comprises administration of a second dosage comprising clonidine, hydroxyzine, ondansetron and naltrexone. In a preferred embodiment, the method comprises administration of a first dosage comprising clonidine, hydroxyzine and ondansetron and administration of a second dosage comprising clonidine, hydroxyzine, ondansetron and naltrexone.

In one embodiment, the method comprises administration of the series of self tapering dosages for a period of at least 5 to at long as 20 days. In an embodiment, the method comprises administration of the series of self tapering dosages for a period of at least 7 to 14 days. In another embodiment, the method comprises administration of the series of self tapering dosages for a period of at least 7 to as long as 10 days. The self-tapering dosages can be administered over 5 days, 6 days, 7 days, 8, days, 9 days, 10 days, 11 days, 12 days, 13 days, 14 days, 15 days, 16 days, 17 days, 18 days, 19 days, or 20 days. Preferably, the self-tapering dosages can be administered over 7, 10, or 14 days.

In one embodiment, the method comprises administration of the first dosage after the termination of the patient's opioid pain therapy and lasting for at least 7 days after the termination of opioid pain therapy. In another embodiment, the method comprises administration of the first dosage after the termination of the patient's opioid pain therapy and lasting for 7 days after the termination of opioid pain therapy. In another embodiment, the method comprises administration of the first dosage after the termination of the patient's opioid pain therapy and lasting for at least 1 day after the termination of opioid pain therapy. In another embodiment, the method comprises administration of the first dosage after the termination of the patient's opioid pain therapy and lasting for at least 3 days after the termination of opioid pain therapy. In another embodiment, method comprises administration of the first dosage after the termination of the patient's opioid pain therapy and lasting for 1 to 7 days after the termination of opioid pain therapy, including 1 day, 2 days, 3 days, 4 days, 5 days, 6 days or 7 days. In another embodiment, the method comprises administration of the first dosage after the termination of the patient's opioid pain therapy and lasting for 3 to 7 days after the termination of opioid pain therapy, including 3 days, 4 days, 5 days, 6 days or 7 days.

In one embodiment, the method comprises administration of the first dosage after the termination of the patient's opioid pain therapy within 24 to 72 hours of the last dose of opioid pain medication. In a preferred embodiment, the method comprises administration of the first dosage after the termination of the patient's opioid pain therapy within about 4 to about 12 hours of the last dose of opioid pain medication.

In an embodiment of any of the above methods, the method further comprises administration of a second dosage after the last dose of the first dosage and lasting for at least 16 days after the last dose of the first dosage. In one embodiment, the method further comprises administration of a second dosage after the last dose of the first dosage and lasting for at least 2 days after the last dose of the first dosage. In one embodiment, the method further comprises administration of a second dosage after the last dose of the first dosage and lasting for 2 to 16 days after the last dose of the first dosage, including 3 days, 4 days, 5 days, 6 days, 7 days, 8 days, 9 days, 10 days, 11 days, 12 days, 13 days, 14 days, 15 days or 16 days after the last dose of the first dosage. In some embodiments, the number of days of administration of the first dosage and the number of days of administration of the second dosage are about equal.

In an embodiment of any of the above methods, the method further comprises administration of a second dosage after the last dose of the first dosage, wherein the first dose of the second dosage is administered within 24 hours after the last dose of the first dosage. In one embodiment, the method comprises administration of the second dosage within 8 hours after the last dose of the first dosage. In one embodiment, the method comprises administration of the second dosage within 4 hours after the last dose of the first dosage. In one embodiment, the method comprises administration of the second dosage within 4-12 hours after the last dose of the first dosage. In one embodiment, the method comprises administration of the second dosage within 4-8 hours after the last dose of the first dosage. In one embodiment, the method comprises administration of the second dosage within 8-12 hours after the last dose of the first dosage.

In an embodiment of any of the above methods, the method comprises administration of a first dosage comprising clonidine, hydroxyzine and ondansetron. In one embodiment, the method comprises administration of a first dosage comprising about 0.025 mg to about 3 mg clonidine, about 5 mg to about 100 mg hydroxyzine, and about 0.5 to about 10 mg ondansetron. In another embodiment, the method comprises administration of a first dosage comprising about 0.05 to about 1.0 mg clonidine, about 25 to about 100 mg hydroxyzine, and about 2.5 to about 7.5 mg ondansetron. In another embodiment, the method comprises administration of a first dosage comprising about 20 mg to about 100 mg hydroxyzine, about 0.05 mg to about 2 mg clonidine, and about 2 to about 8 mg ondansetron. In another embodiment, the method comprises administration of a first dosage comprising about 30 mg to about 45 mg hydroxyzine, about 0.5 mg to about 1.0 mg clonidine, and about 2 mg to about 6 mg ondansetron. In a preferred embodiment, the method comprises administration of a first dosage comprising about 37.5 mg hydroxyzine, about 0.1 mg clonidine, and about 4 mg ondansetron.

In an embodiment of any of the above methods, the method comprises administration of a second dosage comprising clonidine, hydroxyzine, ondansetron and naltrexone. In one embodiment, the method comprises administration of a second dosage comprising about 0.025 mg to about 3 mg clonidine, about 5 mg to about 100 mg hydroxyzine, about 0.5 to about 10 mg ondansetron, and about 0.25 to about 50 mg naltrexone. In another embodiment, the method comprises administration of a second dosage comprising about 0.05 to about 1.0 mg clonidine, about 25 to about 100 mg hydroxyzine, about 2.5 to about 7.5 mg ondansetron, and about 0.05 to about 2.0 mg naltrexone. In another embodiment, the method comprises administration of a second dosage comprising about 15 mg to about 100 mg hydroxyzine, about 0.05 mg to about 2 mg clonidine, about 2 mg to about 8 mg ondansetron, and about 0.5 mg to about 15 mg naltrexone. In another embodiment, the method comprises administration of a second dosage comprising about 20 mg to about 30 mg hydroxyzine, about 0.05 mg to about 1 mg clonidine, about 2 mg to about 6 mg ondansetron, and 1 mg naltrexone. In a preferred embodiment, the method comprises administration of a second dosage comprising about 25 mg hydroxyzine, about 0.1 mg clonidine, about 4 mg ondansetron, and about 1 mg naltrexone.

In a particularly preferred embodiment of any of the above methods, the method comprises administration of a first dosage comprising about 37.5 mg hydroxyzine, about 0.1 mg clonidine, and about 4 mg ondansetron, and administration of a second dosage comprising about 25 mg hydroxyzine, about 0.1 mg clonidine, about 4 mg ondansetron, and about 1 mg naltrexone.

In any of the above embodiments, the method may comprise administering more than one dose of the first dosage per day. In any of the above embodiments, the method may comprise administering more than one dose of the second dosage per day. In any of the above embodiments, the first dosage is administered at least once per day. In any of the above embodiments, the second dosage is administered at least once per day.

In any of the above embodiments, the method may comprise administering a first dosage wherein the amount of one or more of hydroxyzine, clonidine, and ondansetron varies from earlier doses to later doses. In a preferred embodiment, the method may comprise administering a first dosage wherein the amount of one or more of hydroxyzine, clonidine, and ondansetron decreases from earlier doses to later doses.

In any of the above embodiments, the method may comprise administering a second dosage wherein the amount of one or more of hydroxyzine, clonidine, ondansetron and naltrexone varies from earlier doses to later doses. In a preferred embodiment, the method may comprise administering a second dosage wherein the amount of one or more of hydroxyzine, clonidine, and ondansetron decreases from earlier doses to later doses. In another preferred embodiment, the method may comprise administering a second dosage wherein the amount of naltrexone increases from earlier doses to later doses.

In any of the above embodiments, the method may comprise administering a first dosage comprising a ratio of hydroxyzine to clonidine to ondansetron in the first dosage form is about 7.5 to about 22.5 wt % hydroxyzine: about 0.008 to about 1 wt % clonidine: about 1 to about 3 wt % ondansetron.

In any of the above embodiments, the method may comprise administering a second dosage comprising a ratio of hydroxyzine to clonidine to ondansetron to naltrexone in the second dosage form is about 1 to about 80 wt % hydroxyzine: about 0.33 to about 40 wt % clonidine: about 0.133 to about 12 wt % ondansetron: about 1 to about 30 wt % naltrexone.

In any of the above embodiments, the method comprises administering therapeutically effective amounts of the dosages as discussed herein. In any of the above embodiments, methods of administering therapeutically effective amounts of the dosages of the disclosure at a flat dose are provided. A flat dose is a particular amount of a therapeutically active ingredient (e.g., hydroxyzine, clonidine, ondansetron and naloxone) that is administered to every patient regardless of weight. Depending on the type and severity of the patient's symptoms, a flat dose of the therapeutically active ingredients as described herein is administered to the patient. The physician administering treatment will be able to determine the appropriate dose for the individual subject for flat dosing based on the type and severity of the symptoms. Alternatively, the physician administering treatment will be able to determine the appropriate dose for the individual subject for body weight-based dosing based on the type and severity of the symptoms in combination with the patient's body weight. Note that while a dose may be flat, the treatment across different dosages, e.g. from a first dosage to a second dosage, can be different from each other.

Dosage Packages of the Disclosure

In another aspect of the present disclosure, there is provided a self tapering dosage package comprising at least two dosages (FIGS. 1-4). In one embodiment, the dosage package comprises a first dosage of a first formulation and a second dosage of a second formulation. In a further embodiment, the first dosage is administered prior to the second dosage, and the first dosage is administered at a patient's termination of opioid pain therapy. In any of the below embodiments, the dosages are configured to alleviate or prevent symptoms of the patient's termination of opioid pain therapy.

Figure 2:
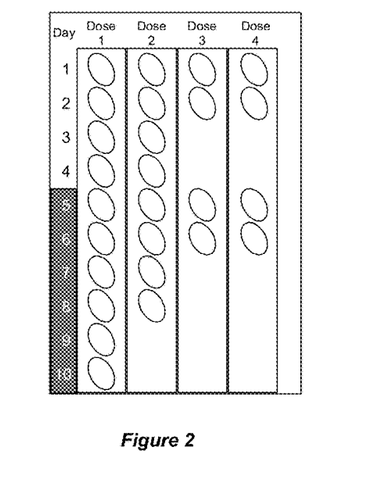
FIG. 2 depicts another exemplary dosage pack according to the disclosure.
Figure 3:
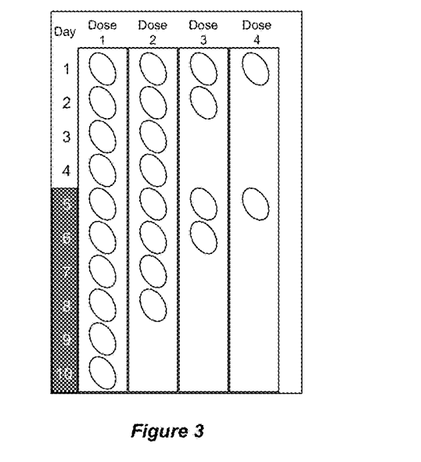
FIG. 3 depicts another exemplary dosage pack according to the disclosure.
Figure 4:
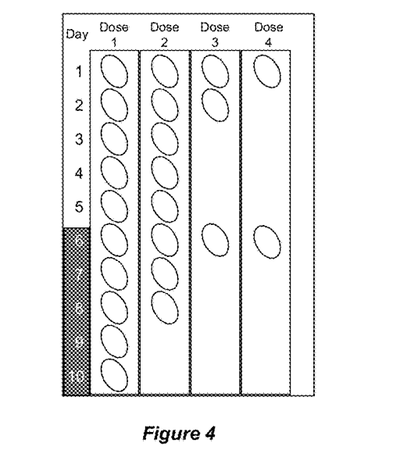
FIG. 4 depicts another exemplary dosage pack according to the disclosure.

In a preferred embodiment, the dosage package is to be administered over the course of the therapeutic method described herein. The dosage package therefore comprises all of the dosages to be administered, and preferably the dosages are separated into at least a first dosage and a second dosage. In a further preferred embodiment, one portion of the dosage pack comprises the first dosage of the first formulation, and a second portion of the dosage pack comprises the second dosage of the second formulation. It is further preferred that the portions of the dosage pack are further separated by the appropriate number of days of the first and second dosage, e.g., if the patient is to receive seven days of the first dosage and ten days of the second dosage, the first portion of the dosage package will comprise seven sub-portions for the first dosage and the second portion of the dosage package will comprise ten sub-portions for the second dosage. It is contemplated herein that multiple doses of at least one of the first dosage or second dosage will be present in the dosage pack, and that different numbers of doses of either the first dosage or second dosage may be given per day (as shown in FIGS. 2-4). In such an embodiment, the daily doses are preferably grouped together, e.g., if four doses are to be given on the first day, three doses on the second day, two doses on the third day, and one dose each subsequent day for the remainder of the duration of administration of the dosage, then the dosage package will comprise, in the appropriate first or second dosage portion, a sub-portion including the four doses for day 1, a different sub-portion including the three doses for day 2, a different sub-portion including the two doses for day 3, and a different sub-portion for each of the single doses for the remaining dosage period.

Figure 1:
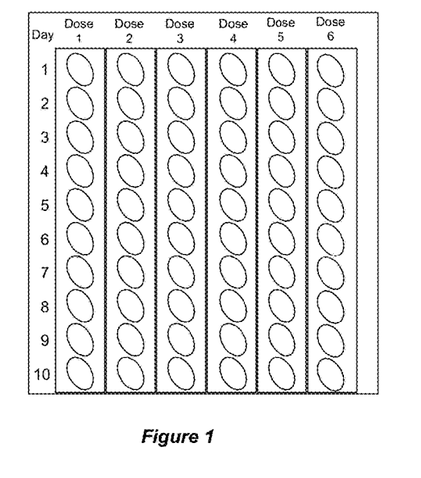
FIG. 1 depicts an exemplary dosage pack according to the disclosure.

In one embodiment, the dosage package comprises two dosages (FIG. 1). In a further embodiment, the first dosage comprises a first pharmaceutical formulation comprising hydroxyzine, clonidine and ondansetron, and the second dosage comprises a second pharmaceutical formulation comprising hydroxyzine, clonidine, ondansetron and naloxone.

In one embodiment, the dosage package comprises a series of self tapering dosages for a period of at least 5 to as long as 20 days. In another embodiment, the dosage package comprises a series of self tapering dosages for a period of at least 7 to as long as 14 days. In another embodiment, the dosage package comprises a series of self tapering dosages for a period of at least 7 to as long as 10 days. The dosage package can be administered over 5 days, 6 days, 7 days, 8, days, 9 days, 10 days, 11 days, 12 days, 13 days, 14 days, 15 days, 16 days, 17 days, 18 days, 19 days, or 20 days. Preferably, the self-tapering dosages can be administered over 7, 10, or 14 days.

In one embodiment, the dosage package comprises at least 7 days of the first dosage. In another embodiment, the dosage package comprises 7 days of the first dosage. In another embodiment, the dosage package comprises at least 1 day of the first dosage. In another embodiment, the dosage package comprises at least 3 days of the first dosage. In another embodiment, the dosage package comprises 1 to 7 days of the first dosage, including 1 day, 2 days, 3 days, 4 days, 5 days, 6 days or 7 days. In a preferred embodiment, the dosage package comprises 3 to 7 days of the first dosage, including 3 days, 4 days, 5 days, 6 days or 7 days.

In one embodiment, the dosage package is administered after the termination of the patient's opioid pain therapy. In a further embodiment, the first dose of the first dosage is administered within 24 to 72 hours of the last dose of opioid pain medication. In a preferred embodiment, the first dose of the first dosage is administered within about 4 to about 12 hours of the last dose of opioid pain medication.

In an embodiment of any of the above dosage packages, the dosage package further comprises at most 16 days of a second dosage. In one embodiment, the dosage package further comprises at least 2 days of the second dosage. In one embodiment, the dosage package further comprises 2 to 16 days of the second dosage, including 3 days, 4 days, 5 days, 6 days, 7 days, 8 days, 9 days, 10 days, 11 days, 12 days, 13 days, 14 days, 15 days or 16 days after the last dose of the first dosage. In some embodiments, the number of days of administration of the first dosage and the number of days of administration of the second dosage are about equal.

In an embodiment of any of the above dosage packages, the dosage package is configured to enable administration of a second dosage after the last dose of the first dosage. In some embodiments, the dosage package does not include the first and second dosages on the same day. In other embodiments, the first dose of the second dosage is administered within 24 hours after the last dose of the first dosage. In one embodiment, the second dosage is administered within 8 hours after the last dose of the first dosage. In one embodiment, the second dosage is administered within 4 hours after the last dose of the first dosage. In one embodiment, the second dosage is administered within 4-12 hours after the last dose of the first dosage. In one embodiment, the second dosage is administered within 4-8 hours after the last dose of the first dosage. In one embodiment, the second dosage is administered within 8-12 hours after the last dose of the first dosage.

In an embodiment of any of the above dosage packages, the dosage package comprises a first dosage comprising clonidine, hydroxyzine and ondansetron. In one embodiment, the dosage package comprises a first dosage comprising about 0.025 mg to about 3 mg clonidine, about 5 mg to about 100 mg hydroxyzine, and about 0.5 to about 10 mg ondansetron. In another embodiment, the dosage package comprises a first dosage comprising about 0.05 to about 1.0 mg clonidine, about 25 to about 100 mg hydroxyzine, and about 2.5 to about 7.5 mg ondansetron. In another embodiment, the dosage package comprises a first dosage comprising about 20 mg to about 100 mg hydroxyzine, about 0.05 mg to about 2 mg clonidine, and about 2 to about 8 mg ondansetron. In another embodiment, the dosage package comprises a first dosage comprising about 30 mg to about 45 mg hydroxyzine, about 0.5 mg to about 1.0 mg clonidine, and about 2 mg to about 6 mg ondansetron. In a preferred embodiment, the dosage package comprises a first dosage comprising about 37.5 mg hydroxyzine, about 0.1 mg clonidine, and about 4 mg ondansetron.

In an embodiment of any of the above dosage packages, the dosage package comprises a second dosage comprising clonidine, hydroxyzine, ondansetron and naltrexone. In one embodiment, the dosage package comprises a second dosage comprising about 0.025 mg to about 3 mg clonidine, about 5 mg to about 100 mg hydroxyzine, about 0.5 to about 10 mg ondansetron, and about 0.25 to about 50 mg naltrexone. In another embodiment, the dosage package comprises a second dosage comprising about 0.05 to about 1.0 mg clonidine, about 25 to about 100 mg hydroxyzine, about 2.5 to about 7.5 mg ondansetron, and about 0.05 to about 2.0 mg naltrexone. In another embodiment, the dosage package comprises a second dosage comprising about 15 mg to about 100 mg hydroxyzine, about 0.05 mg to about 2 mg clonidine, about 2 mg to about 8 mg ondansetron, and about 0.5 mg to about 15 mg naltrexone. In another embodiment, the dosage package comprises a second dosage comprising about 20 mg to about 30 mg hydroxyzine, about 0.05 mg to about 1 mg clonidine, about 2 mg to about 6 mg ondansetron, and 1 mg naltrexone. In a preferred embodiment, the dosage package comprises a second dosage comprising about 25 mg hydroxyzine, about 0.1 mg clonidine, about 4 mg ondansetron, and about 1 mg naltrexone.

In a particularly preferred embodiment of any of the above dosage packages, the dosage package comprises a first dosage comprising about 37.5 mg hydroxyzine, about 0.1 mg clonidine, and about 4 mg ondansetron, and a second dosage comprising about 25 mg hydroxyzine, about 0.1 mg clonidine, about 4 mg ondansetron, and about 1 mg naltrexone.

In an embodiment of any of the above dosage packages, the dosage package comprises at least one first dosage for at least one day. In another embodiment of any of the above dosage packages, the dosage package comprises one or more doses of the first dosage for each day. In another embodiment of any of the above dosage packages, the dosage package can contain multiple doses of the first dosage for a given day in the first dosage portion. In a further embodiment, subsequent days have fewer numbers of doses of the first dosage in the first dosage portion. In another embodiment of any of the above dosage packages, the dosage package comprises at least one second dosage for at least one day. In another embodiment of any of the above dosage packages, the dosage package comprises one or more doses of the second dosage for each day. In another embodiment of any of the above dosage packages, the dosage package can contain multiple doses of the second dosage for a given day in the second dosage portion. In a further embodiment, subsequent days have fewer numbers of doses of the second dosage in the first second portion.

In any of the above embodiments, the dosage package may comprise a first dosage wherein the amount of one or more of hydroxyzine, clonidine, and ondansetron varies from earlier doses to later doses. In a preferred embodiment, the dosage package may comprise a first dosage wherein the amount of one or more of hydroxyzine, clonidine, and ondansetron decreases from earlier doses to later doses.

In any of the above embodiments, the dosage package may comprise a second dosage wherein the amount of one or more of hydroxyzine, clonidine, ondansetron and naltrexone varies from earlier doses to later doses. In a preferred embodiment, the dosage package may comprise a second dosage wherein the amount of one or more of hydroxyzine, clonidine, and ondansetron decreases from earlier doses to later doses. In another preferred embodiment, the dosage package may comprise administering a second dosage wherein the amount of naltrexone increases from earlier doses to later doses.

In any of the above embodiments, the dosage package may comprise a first dosage comprising a ratio of hydroxyzine to clonidine to ondansetron in the first dosage form is about 7.5 to about 22.5 wt % hydroxyzine: about 0.008 to about 1 wt % clonidine: about 1 to about 3 wt % ondansetron.

In any of the above embodiments, the dosage package may comprise a second dosage comprising a ratio of hydroxyzine to clonidine to ondansetron to naltrexone in the second dosage form is about 1 to about 80 wt % hydroxyzine: about 0.33 to about 40 wt % clonidine: about 0.133 to about 12 wt % ondansetron: about 1 to about 30 wt % naltrexone.

In any of the above embodiments, the dosage package comprises therapeutically effective amounts of the dosages as discussed herein. In any of the above embodiments, the dosage package comprises therapeutically effective amounts of the dosages of the disclosure at a flat dose. A flat dose is a particular amount of a therapeutically active ingredient (e.g., hydroxyzine, clonidine, ondansetron and naloxone) that is administered to every patient regardless of weight. Depending on the type and severity of the patient's symptoms, a flat dose of the therapeutically active ingredients as described herein is administered to the patient. The physician administering treatment will be able to determine the appropriate dose for the individual subject for flat dosing based on the type and severity of the symptoms. Alternatively, the physician administering treatment will be able to determine the appropriate dose for the individual subject for body weight-based dosing based on the type and severity of the symptoms in combination with the patient's body weight.

Pharmaceutical Compositions of the Disclosure

In another aspect of the present disclosure, there is provided a pharmaceutical composition comprising at least three of hydroxyzine, clonidine, ondansetron and naltrexone. In a preferred embodiment, the pharmaceutical composition is formulated into a single unit dosage, wherein the single unit dosage is administered to a patient at termination of the patient's opioid pain therapy. As discussed herein, the single unit dosage is preferably (but not exclusively) a single tablet or capsule comprising a compounded pharmaceutical composition comprising at least three of hydroxyzine, clonidine, ondansetron and naltrexone. It is further contemplated herein that the single tablet or capsule may contain varying amounts of one or more of hydroxyzine, clonidine, ondansetron and naltrexone. It is further contemplated herein that the pharmaceutical compositions of the disclosure are included within a dosage pack as described herein. It is also contemplated that the pharmaceutical compositions of the disclosure are formulated into other dosage forms (e.g., for topical, rectal, mucosal, sublingual, nasal, naso/oro-gastric gavage, parenteral, intraperitoneal, intradermal, transdermal, intrathecal, nasal, and intracheal administration) as discussed in further detail below.

In one embodiment, the pharmaceutical composition comprises a series of tapering dosages of at least one of hydroxyzine, clonidine, ondansetron and naltrexone.

In one embodiment, the pharmaceutical composition is provided in a dosage package comprising at least two dosages. In a further embodiment, the first dosage comprises hydroxyzine, clonidine and ondansetron, and the second dosage comprises hydroxyzine, clonidine, ondansetron and naloxone.

In one embodiment, the pharmaceutical composition comprises a series of self tapering dosages to be administered over a period of at least 5 to as long as 20 days. In another embodiment, the pharmaceutical composition comprises a series of self tapering dosages to be administered over a period of at least 7 to as long as 14 days. In another embodiment, the pharmaceutical composition comprises a series of self tapering dosages to be administered over a period of at least 7 to as long as 10 days. The pharmaceutical composition can be administered over 5 days, 6 days, 7 days, 8, days, 9 days, 10 days, 11 days, 12 days, 13 days, 14 days, 15 days, 16 days, 17 days, 18 days, 19 days, or 20 days. Preferably, the pharmaceutical composition can be administered over 7, 10, or 14 days.

In one embodiment, the pharmaceutical composition comprises a first dosage to be administered over a period of at least 7 days. In another embodiment, the pharmaceutical composition comprises a first dosage to be administered over a period of at least 1 day. In another embodiment, the pharmaceutical composition comprises a first dosage to be administered over a period of at least 3 days. In another embodiment, the pharmaceutical composition comprises a first dosage to be administered over a period of at least 1 to as long as 7 days of the first dosage, including 1 day, 2 days, 3 days, 4 days, 5 days, 6 days or 7 days. In a preferred embodiment, the pharmaceutical composition comprises at least 3 to as long as 7 days of the first dosage, including 3 days, 4 days, 5 days, 6 days or 7 days.

In one embodiment, the first dosage of the pharmaceutical composition is administered after the termination of the patient's opioid pain therapy. In a further embodiment, the first dose of the first dosage is administered within 24 to 72 hours of the last dose of opioid pain medication. In a preferred embodiment, the first dose of the first dosage is administered within about 4 to about 12 hours of the last dose of opioid pain medication.

In an embodiment of any of the above pharmaceutical compositions, the pharmaceutical composition further comprises a second dosage to be administered over at most 16 days. In one embodiment, the pharmaceutical composition further comprises a second dosage to be administered over at least 2 days. In one embodiment, the pharmaceutical composition further comprises a second dosage to be administered over at least 2 to as long as 16 days, including 3 days, 4 days, 5 days, 6 days, 7 days, 8 days, 9 days, 10 days, 11 days, 12 days, 13 days, 14 days, 15 days or 16 days after the last dose of the first dosage. In some embodiments, the number of days of administration of the first dosage and the number of days of administration of the second dosage are about equal.

In an embodiment of any of the above pharmaceutical compositions, the first dose of the second dosage of the pharmaceutical composition is administered after the last dose of the first dosage. In some embodiments, the first and second dosages of the pharmaceutical composition are not administered on the same day. In other embodiments, the first dose of the second dosage is administered within 24 hours after the last dose of the first dosage. In one embodiment, the second dosage is administered within 8 hours after the last dose of the first dosage. In one embodiment, the second dosage is administered within 4 hours after the last dose of the first dosage. In one embodiment, the second dosage is administered within 4-12 hours after the last dose of the first dosage. In one embodiment, the second dosage is administered within 4-8 hours after the last dose of the first dosage. In one embodiment, the second dosage is administered within 8-12 hours after the last dose of the first dosage.

In an embodiment of any of the above pharmaceutical compositions, the pharmaceutical composition comprises a first dosage comprising clonidine, hydroxyzine and ondansetron. In one embodiment, the pharmaceutical composition comprises a first dosage comprising about 0.025 mg to about 3 mg clonidine, about 5 mg to about 100 mg hydroxyzine, and about 0.5 to about 10 mg ondansetron. In another embodiment, the pharmaceutical composition comprises a first dosage comprising about 0.05 to about 1.0 mg clonidine, about 25 to about 100 mg hydroxyzine, and about 2.5 to about 7.5 mg ondansetron. In another embodiment, the pharmaceutical composition comprises a first dosage comprising about 20 mg to about 100 mg hydroxyzine, about 0.05 mg to about 2 mg clonidine, and about 2 to about 8 mg ondansetron. In another embodiment, the pharmaceutical composition comprises a first dosage comprising about 30 mg to about 45 mg hydroxyzine, about 0.5 mg to about 1.0 mg clonidine, and about 2 mg to about 6 mg ondansetron. In a preferred embodiment, the pharmaceutical composition comprises a first dosage comprising about 37.5 mg hydroxyzine, about 0.1 mg clonidine, and about 4 mg ondansetron.

In an embodiment of any of the above pharmaceutical compositions, the pharmaceutical composition comprises a second dosage comprising clonidine, hydroxyzine, ondansetron and naltrexone. In one embodiment, the pharmaceutical composition comprises a second dosage comprising about 0.025 mg to about 3 mg clonidine, about 5 mg to about 100 mg hydroxyzine, about 0.5 to about 10 mg ondansetron, and about 0.25 to about 50 mg naltrexone. In another embodiment, the pharmaceutical composition comprises a second dosage comprising about 0.05 to about 1.0 mg clonidine, about 25 to about 100 mg hydroxyzine, about 2.5 to about 7.5 mg ondansetron, and about 0.05 to about 2.0 mg naltrexone. In another embodiment, the pharmaceutical composition comprises a second dosage comprising about 15 mg to about 100 mg hydroxyzine, about 0.05 mg to about 2 mg clonidine, about 2 mg to about 8 mg ondansetron, and about 0.5 mg to about 15 mg naltrexone. In another embodiment, the dosage package comprises a second dosage comprising about 20 mg to about 30 mg hydroxyzine, about 0.05 mg to about 1 mg clonidine, about 2 mg to about 6 mg ondansetron, and 1 mg naltrexone. In a preferred embodiment, the pharmaceutical composition comprises a second dosage comprising about 25 mg hydroxyzine, about 0.1 mg clonidine, about 4 mg ondansetron, and about 1 mg naltrexone.

In a particularly preferred embodiment of any of the above pharmaceutical compositions, the pharmaceutical composition comprises a first dosage comprising about 37.5 mg hydroxyzine, about 0.1 mg clonidine, and about 4 mg ondansetron, and a second dosage comprising about 25 mg hydroxyzine, about 0.1 mg clonidine, about 4 mg ondansetron, and about 1 mg naltrexone.

In an embodiment of any of the above pharmaceutical compositions, the pharmaceutical composition comprises at least one first dosage for at least one day. In another embodiment of any of the above pharmaceutical compositions, the pharmaceutical composition comprises one or more doses of the first dosage for each day. In another embodiment of any of the above pharmaceutical compositions, multiple doses of the first dosage of the pharmaceutical composition may be administered on a given day. In a further embodiment, fewer doses of the of the first dosage of the pharmaceutical composition are administered over subsequent days. In an embodiment of any of the above pharmaceutical compositions, the pharmaceutical composition comprises at least one second dosage for at least one day. In another embodiment of any of the above pharmaceutical compositions, the pharmaceutical composition comprises one or more doses of the second dosage for each day. In another embodiment of any of the above pharmaceutical compositions, multiple doses of the second dosage of the pharmaceutical composition may be administered on a given day. In a further embodiment, fewer doses of the second dosage of the pharmaceutical composition are administered over subsequent days.

In any of the above embodiments, the pharmaceutical composition may comprise a first dosage wherein the amount of one or more of hydroxyzine, clonidine, and ondansetron varies from earlier doses to later doses. In a preferred embodiment, the pharmaceutical composition may comprise a first dosage wherein the amount of one or more of hydroxyzine, clonidine, and ondansetron decreases from earlier doses to later doses.

In any of the above embodiments, the pharmaceutical composition may comprise a second dosage wherein the amount of one or more of hydroxyzine, clonidine, ondansetron and naltrexone varies from earlier doses to later doses. In a preferred embodiment, the pharmaceutical composition may comprise a second dosage wherein the amount of one or more of hydroxyzine, clonidine, and ondansetron decreases from earlier doses to later doses. In another preferred embodiment, the pharmaceutical composition may comprise a second dosage wherein the amount of naltrexone increases from earlier doses to later doses.

In any of the above embodiments, the pharmaceutical composition may comprise a first dosage comprising a ratio of hydroxyzine to clonidine to ondansetron in the first dosage form is about 7.5 to about 22.5 wt % hydroxyzine: about 0.008 to about 1 wt % clonidine: about 1 to about 3 wt % ondansetron.

23. In any of the above embodiments, the pharmaceutical composition may comprise a second dosage comprising a ratio of hydroxyzine to clonidine to ondansetron to naltrexone in the second dosage form is about 1 to about 80 wt % hydroxyzine: about 0.33 to about 40 wt % clonidine: about 0.133 to about 12 wt % ondansetron: about 1 to about 30 wt % naltrexone.

In any of the above embodiments, the pharmaceutical composition comprises therapeutically effective amounts of the dosages as discussed herein. In any of the above embodiments, the pharmaceutical composition comprises therapeutically effective amounts of the dosages of the disclosure at a flat dose. A flat dose is a particular amount of a therapeutically active ingredient (e.g., hydroxyzine, clonidine, ondansetron and naloxone) that is administered to every patient regardless of weight. Depending on the type and severity of the patient's symptoms, a flat dose of the therapeutically active ingredients as described herein is administered to the patient. The physician administering treatment will be able to determine the appropriate dose for the individual subject for flat dosing based on the type and severity of the symptoms. Alternatively, the physician administering treatment will be able to determine the appropriate dose for the individual subject for body weight-based dosing based on the type and severity of the symptoms in combination with the patient's body weight.

Formulations Comprising the Pharmaceutical Compositions of the Disclosure

The compositions of the disclosure can comprise a carrier and/or excipient. While it is possible to use a compound of the present disclosure for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, sterilized human milk, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Those of relevant skill in the art are well able to prepare suitable solutions.

In one embodiment of any of the compositions of the disclosure, the composition is formulated for delivery by a route such as, e.g., oral, topical, rectal, mucosal, sublingual, nasal, naso/oro-gastric gavage, parenteral, intraperitoneal, intradermal, transdermal, intrathecal, nasal, and intracheal administration. In one embodiment of any of the compositions of the disclosure, the composition is in a form of a liquid, foam, cream, spray, powder, or gel. In one embodiment of any of the compositions of the disclosure, the composition comprises a buffering agent (e.g., sodium bicarbonate, infant formula or sterilized human milk). In a preferred embodiment, the composition is formulated for oral delivery.

Administration of the compounds and compositions in the methods of the disclosure can be accomplished by any method known in the art. Non-limiting examples of useful routes of delivery include oral, rectal, fecal (by enema), and via naso/oro-gastric gavage, as well as parenteral, intraperitoneal, intradermal, transdermal, intrathecal, nasal, and intracheal administration. The active agent may be systemic after administration or may be localized by the use of regional administration, intramural administration, or use of an implant that acts to retain the active dose at the site of implantation. The carrier material should be non-toxic to the bacteria and the subject/patient.

Although there are no physical limitations to delivery of the formulations of the present disclosure, oral delivery is preferred for delivery to the digestive tract because of its ease and convenience, and because oral formulations readily accommodate additional mixtures and multiple pharmaceutically active ingredients.

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance. In a preferred embodiment, the active ingredient(s) are compounded and administered in a single tablet or capsule.

Formulations suitable for parenteral administration include aqueous and nonaqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity, such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN® 80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, croscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants, such as fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes, such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances, such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an inhibitor of Nt5e or A1R is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

The inventive composition or pharmaceutically acceptable derivatives thereof may be formulated as aerosols for application e.g., by inhalation or intranasally (e.g., as described in U.S. Pat. Nos. 4,044,126, 4,414,209, and 4,364,923). These formulations can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be also formulated for local or topical application, such as for application to the skin and mucous membranes (e.g., intranasally), in the form of nasal solutions, gels, creams, and lotions.

Other routes of administration, such as transdermal patches are also contemplated herein. Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1

In any of the foregoing methods, dosage packages, or pharmaceutical compositions, the first dosage included:
37.5 mg hydroxyzine, 0.1 mg clonidine, and 4 mg ondansetron, and the second dosage included:
25 mg hydroxyzine, 0.1 mg clonidine, 4 mg ondansetron, and 1 mg naltrexone.

Example 2

In any of the foregoing methods, dosage packages, or pharmaceutical compositions, the first dosage includes:
56.25 mg hydroxyzine, 0.15 mg clonidine, and 6 mg ondansetron, and the second dosage includes:
37.5 mg hydroxyzine, 0.15 mg clonidine, 6 mg ondansetron, and 1.5 mg naltrexone.

Example 3

In any of the foregoing methods, dosage packages, or pharmaceutical compositions, the first dosage includes:
26.25 mg hydroxyzine, 0.07 mg clonidine, and 2.8 mg ondansetron, and the second dosage includes:
17.5 mg hydroxyzine, 0.07 mg clonidine, 2.8 mg ondansetron, and 0.7 mg naltrexone.

Example 4

In any of the foregoing methods, dosage packages, or pharmaceutical compositions, the first dosage includes:
30 mg to 45 mg hydroxyzine, 0.5 mg to 1.0 mg clonidine, and 2 mg to 6 mg ondansetron, and the second dosage includes:
20 mg to 30 mg hydroxyzine, 0.05 mg to 1.0 mg clonidine, 2 mg to 6 mg ondansetron, and 1 mg naltrexone.

Example 5

In any of the foregoing methods, dosage packages, or pharmaceutical compositions, the first dosage includes:
20 mg to 100 mg hydroxyzine, 0.05 mg to 2.0 mg clonidine, and 2 mg to 8 mg ondansetron,
and the second dosage includes:
15 mg to 100 mg hydroxyzine, 0.05 mg to 2.0 mg clonidine, 2 mg to 8 mg ondansetron, and 0.5 mg to 15 mg naltrexone.

Example 6

In any of the foregoing methods, dosage packages, or pharmaceutical compositions, the pharmaceutical composition includes at least three of:
25 mg to 100 mg hydroxyzine, 0.025 mg to 3.0 mg clonidine, 0.5 mg to 10 mg ondansetron and 0.25 to 50 mg naltrexone.

Example 7

In any of the foregoing methods or pharmaceutical compositions, a first dosage and a second dosage are preferably included in a dosage package as described herein. It is contemplated herein that multiple doses of each of the first and second dosage can be included in the dosage pack, as exemplarily shown in FIG. 1. It is further contemplated herein that different numbers of doses of each of the first and second dosage can be included in the dosage pack, as exemplarily shown in FIGS. 2-4. The numbers of doses of each of the first and second dosage can decrease over time, as exemplarily shown in FIGS. 2-4. Further, the numbers of doses of the first dosage can be different from the numbers of doses of the second dosage, as exemplarily shown in FIG. 4.

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present disclosure will be limited only by the appended claims and equivalents thereof. The scope of the disclosure is therefore indicated by the following claims, rather than the foregoing description and above-discussed embodiments, and all changes that come within the meaning and range of equivalents thereof are intended to be embraced therein.

All patents, applications, publications, test methods, literature, and other materials cited herein are hereby incorporated by reference in their entirety as if physically present in this specification.

What is claimed is:

1. A self-tapering dosage package, wherein the dosage package comprises a first dosage of a first formulation and a second dosage of a second formulation for administering after the first dosage,
    wherein the first formulation comprises a dose of hydroxyzine, a dose of clonidine, and a dose of ondansetron in a single unit dosage,
    wherein, the second formulation comprises a tapered dose of hydroxyzine, a tapered dose of clonidine, a tapered dose of ondansetron, and a dose of naltrexone in a single unit dosage, and
    wherein the first and second dosages are configured to alleviate or prevent symptoms of the patient's termination of opioid pain therapy.

2. The dosage package of claim 1, wherein the first dosage comprises a pharmaceutical formulation comprising:
    30 mg to 45 mg hydroxyzine;
    0.5 mg to 1.0 mg clonidine; and
    2 mg to 6 mg ondansetron, and
wherein the second dosage comprises a pharmaceutical formulation comprising:
    20 mg to 30 mg hydroxyzine;
    0.05 mg to 1.0 mg clonidine;
    2 mg to 6 mg ondansetron; and
    1 mg naltrexone.

3. The dosage package of claim 1, wherein the dosage package includes at least three days of the first dosage.

4. The dosage package of claim 3, wherein the dosage package contains at least one first dosage for at least one day.

5. The dosage package of claim 3, wherein the dosage package includes at least two days of the second dosage.

6. The dosage package of claim 5, wherein the dosage package contains at least one second dosage for at least one day.

7. The dosage package of claim 5, wherein the dosage package does not include the first and second dosages on the same day.

8. The dosage package of claim 1, wherein the first dosage comprises:
   20 mg to 100 mg hydroxyzine;
   0.05 mg to 2 mg clonidine; and
   2 mg to 8 mg ondansetron.

9. The dosage package of claim 1, wherein the second dosage comprises:
   15 mg to 100 mg hydroxyzine;
   0.05 mg to 2 mg clonidine;
   2 mg to 8 mg ondansetron; and
   0.5 mg to 15 mg naltrexone.

\* \* \* \* \*